United States Patent
Stangl

(12) 
(10) Patent No.: US 8,183,389 B2
(45) Date of Patent: May 22, 2012

(54) PROCESS FOR THE TREATMENT OF AN AQUEOUS MIXTURE COMPRISING A DIPOLAR APROTIC COMPOUND

(75) Inventor: Jochen Stangl, Wehr (DE)

(73) Assignee: DSM IP Assets B.V., Heerlen (NL)

( * ) Notice: Subject to any disclaimer, the term of this patent is extended or adjusted under 35 U.S.C. 154(b) by 38 days.

(21) Appl. No.: 12/097,653

(22) PCT Filed: Dec. 20, 2006

(86) PCT No.: PCT/EP2006/012331
§ 371 (c)(1),
(2), (4) Date: Oct. 31, 2008

(87) PCT Pub. No.: WO2007/093211
PCT Pub. Date: Aug. 23, 2007

(65) Prior Publication Data
US 2009/0076285 A1    Mar. 19, 2009

(30) Foreign Application Priority Data
Dec. 20, 2005   (EP) ..................................... 05027936

(51) Int. Cl.
C07D 207/267   (2006.01)
C07C 35/18     (2006.01)
C07C 273/16    (2006.01)
C07C 317/04    (2006.01)
C07F 9/28      (2006.01)

(52) U.S. Cl. ............ 548/555; 568/824; 568/27; 564/73; 564/15

(58) Field of Classification Search .................. None
See application file for complete search history.

(56) References Cited

U.S. PATENT DOCUMENTS

| 4,701,555 A | 10/1987 | Young et al. |
| 6,137,004 A | 10/2000 | McQuigg et al. |

FOREIGN PATENT DOCUMENTS

| DE | 152 578 | 12/1981 |
| DE | 268 241 | 5/1989 |
| EP | 0 363 894 | 4/1990 |
| EP | 0 697 396 | 2/1996 |
| WO | 97/13761 | 4/1997 |
| WO | 00/29088 | 5/2000 |
| WO | 03/048183 | 6/2003 |

OTHER PUBLICATIONS

Guenu et al., Journal of Chromatograph A, vol. 737, p. 15-24 (1996).*
Carnerup et al. Toxicology Letters, vol. 162, (2006), p139-145, available online Nov. 29, 2005.*
Database WPI Week 198929, XP002431291—JP 01 149756; Jun. 1989 (Abstract).
Database WPI Week 197733, XP002431292—JP 52 078831, Jul. 1977 (Abstract).
Database WPI Week 197734, XP002431293—JP 48 052735, Jul. 1973 (Abstract).
International Search Report for PCT/EP2006/012331 mailed May 14, 2007.
Written Opinion for PCT/EP2006/012331 mailed May 14, 2007.
Amberlite™ XAD™ Polymeric Adsorbents, Rohm and Haas Company, Jun. 2000.

* cited by examiner

*Primary Examiner* — Yong Chu
(74) *Attorney, Agent, or Firm* — Nixon & Vanderhye P.C.

(57) ABSTRACT

The invention relates to a process for the treatment of an aqueous mixture comprising a dipolar aprotic compound, comprising: a) an adsorption step, in which the aqueous mixture is brought into contact with a porous adsorbent, whereby the porous adsorbent is chosen such that the dipolar aprotic compound adsorbs to it more readily than water; b) a desorption step, in which the porous adsorbent is brought into contact with a desorbing agent, whereby a recovery solution is formed comprising the desorbing agent and the dipolar aprotic compound.

7 Claims, No Drawings

PROCESS FOR THE TREATMENT OF AN AQUEOUS MIXTURE COMPRISING A DIPOLAR APROTIC COMPOUND

The invention relates to a process for the treatment of an aqueous mixture comprising a dipolar aprotic compound, for the purpose of removing the dipolar aprotic compound from the aqueous mixture and preferably the subsequent retrieval of it.

Such a process is known from DE 3834904 A1. In DE 3834904 A1, a process is disclosed for the recovery of N-methyl-2-pyrrolidone (a synonym 1-methyl-2-pyrrolidone, NMP), a dipolar aprotic compound, from an aqueous solution by means of extraction with certain derivatives of phenol such as nonylphenol.

The known extraction process has as disadvantage that the solvents as indicated are undesirable from viewpoint of toxicity and environmental protection.

It is the objective of the present invention to reduce or even eliminate the said disadvantages.

The said objective is achieved in that the process comprises
a) an adsorption step, in which the aqueous mixture is brought into contact with a porous adsorbent, whereby the porous adsorbent is chosen such that the dipolar aprotic compound adsorbs to it more readily than water;
b) a desorption step, in which the porous adsorbent is brought into contact with a desorbing agent, whereby a recovery solution is formed comprising the desorbing agent and the dipolar aprotic compound.

The advantage of the process according to the invention is that it is not necessary to rely on an extraction step and the associated need for specifically chosen extraction compounds to achieve the retrieval of the dipolar aprotic compound. Nevertheless, the process according to the invention can result in the dipolar aprotic compound being retrieved in high percentages, even close to 100%. An additional advantage of the process according to the invention is that a purified aqueous mixture is obtained without residues of extraction agents as in the known process.

The process according to the invention relates to the treatment of an aqueous mixture comprising a dipolar aprotic compound. In the aqueous mixture, which is typically in liquid form, water is a continuous phase; other compounds may also be present, although it is preferred that the amount of compounds that can act as desorbing agent—as discussed in more detail below—is at most 30 wt. %, based on the aqueous mixture as a whole; more preferably this amount is at most 20 or 10 wt. %; most preferably, the amount in the aqueous mixture of compounds that can act as desorbing agent is essentially zero. Examples of other compounds that may be present in the aqueous mixture are electrolytes such as organic or inorganic salts.

The aqueous mixture to be treated in the process according to the invention comprises a dipolar aprotic compound. Such compounds are as such known and are generally recognised to be compounds with a comparatively high dielectric constant, typically greater than about 15, and a sizable permanent dipole moment, that cannot donate suitably labile hydrogen atoms to form strong hydrogen bonds and thus are essentially non-protogenic. Examples of dipolar aprotic compounds that may advantageously be removed from an aqueous mixture in the process according to the invention include the group consisting of hexamethylphosphorous triamide (HMPT), dimethylsulfoxide (DMSO), 1-methyl-2-pyrrolidone (NMP), 1-ethyl-2-pyrrolidone (NEP), and urea derivatives of the following formula (I):

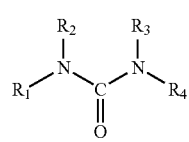

wherein $R_1$, $R_2$, $R_3$ and $R_4$ may each independently be H or a $C_1$-$C_4$ alkyl group and whereby $R_2$ and $R_3$ may be a part of a heterocyclic group. In formula (I), it is preferred that $R_1$, $R_2$, $R_3$ and $R_4$ are each independently H or a methyl or an ethyl group. In another embodiment, it is preferred that $R_1$, $R_2$, $R_3$ and $R_4$ are identical. In another class of preferred embodiments of the compound according to formula (I), $R_2$ and $R_3$ are such that compound (I) comprises a heterocyclic ring. As is known, the term heterocyclic ring indicates a ring structure wherein the ring-forming atoms are not all carbon. Since $R_2$ and $R_3$ will in the case of ring-forming only contribute carbon atoms as ring-forming atoms, this implies that within the context of the present invention the two nitrogen atoms are comprised within the ring structure. If the compound according to formula (I) has a heterocyclic ring, then this ring is preferably a 5- or 6-ring. Preferred examples of compounds according to formula (I) are urea, 1,3-dimethyltetrahydro-2(1H)-pyrimidinone (DMPU) or 1,1,3,3-tetramethylurea (TMU).

The aqueous mixture may contain one dipolar aprotic compound; however the process according to the invention is also applicable in case the aqueous mixture contains several dipolar aprotic compounds as identified above.

The amount of the dipolar aprotic compound in the aqueous mixture may vary within wide limits—as it indeed does in practice. It was found that the benefits of the process according to the invention are particularly visible in cases where the aqueous mixture contains relatively low amounts of the dipolar aprotic compound. In a preferred embodiment, therefore, the aqueous mixture to be treated in the process according to the invention contains at most 40 wt. %, more preferably at most 30, 20, 10 or even at most 8, 6, 5 or even 4 wt. % of dipolar aprotic compound or compounds, based on the total of the aqueous mixture. Surprisingly, the objectives according to the invention are even achieved when aqueous mixtures are treated that comprise at most 2 or 1 wt. % of dipolar aprotic compound or compounds, or even at most 0.5 or 0.1 wt. %.

The process according to the invention comprises an adsorption step. In the adsorption step, the aqueous mixture is brought into contact with a porous adsorbent. A wide variety of porous adsorbents are suitable for use in the process according to the invention, provided that a dipolar aprotic compound adheres to it more readily than water so as to ensure that a reduction or even removal of the dipolar aprotic compound from the aqueous mixture can indeed take place. Whether or not a porous adsorbent fulfils this criterion—i.e. that a dipolar aprotic compound has a higher affinity to it that water—may be easily tested by the skilled person through simple routine tests that are as such known. One such a test comprises the following steps: in a vessel, a composition is made containing a known concentration of a dipolar aprotic compound in a liquid aqueous system. Subsequently, a known quantity of a porous adsorbent is added to the vessel, into the composition. The composition plus adsorbent are then stirred for about one hour. Then, a sample of the composition is taken, and the concentration of the dipolar aprotic compound determined. If the said concentration has decreased, then this is an indicator that the porous adsorbent fulfils the abovementioned criterion. Another test for determining whether a porous adsorbent is suitable for use in the process according to the invention comprises the following steps: a column is filled with the porous adsorbent. A liquid composition—containing a known concentration of a dipolar aprotic compound in a liquid aqueous system—is fed to the top of the column and made to flow through the porous adsorbent. As soon as the composition exits at the bottom of the column, a sample is taken and the concentration of the dipolar aprotic compound determined. If the said concentration has decreased, then this is an indicator that the porous adsorbent fulfils the abovementioned criterion.

Various types of porous adsorbents may be used in the process according to the invention; examples of such types are carbonaceous adsorbents such as activated carbon as well as resin-based adsorbents or adsorbents comprising silica or alumina. Suitable adsorbents may comprise micropores (herein defined as pores having an average diameter of at most 2 nm), mesopores (herein defined as pores having an average diameter lying between 2 and 50 nm), or macropores (herein defined as pores having an average diameter larger than 50 nm), or mixtures thereof. Preferably, the porous adsorbent comprises a mixture of micropores, mesopores and macropores; this has the advantage that a high adsorbing capacity of the adsorbent is combined with a good accessibility of the porous adsorbent for the aqueous mixture. Preferably, resin-based adsorbents are used. As is known, resin-based porous adsorbents are obtainable in non-functionalised form or in functionalised ion-exchange form. For the process according to the invention, preferably porous adsorbents essentially prepared from non-functionalised resins are used. It is advantageous when the said non-functionalised resin has a high specific surface area, of preferably at least 400, 500, 600, 700 or even 800 square meters per gram of adsorbent ($m^2/g$), and is cross-linked. An example of a resin suitable for preparation of the porous adsorbent is a polystyrene-divinylbenzene resin. Such resins and porous adsorbents made therefrom are as such known. Examples of a suitable porous adsorbent based on a cross-linked polystyrene-divinylbenzene resin are Lewatit® VP OC 1163 (Supplier: Lanxess), Amberlite® XAD 4 (supplier: Rohm & Haas), Dowex Optipore® L493 (supplier: Dow Chemical) and Sepabeads® SP700 (supplier: Mitsubishi Chemical Corporation). As indicated, the specific surface area of the porous adsorbent is preferably at least 400, 500, 600, 700 or 800 $m^2/g$; more preferably, the specific surface area is at least 900, 1000, 1100, 1200 or even 1300 $m^2/g$. Although there is according the invention no reason to limit the specific surface area of the porous adsorbent other than that there should remain a physical possibility for the dipolar aprotic compound to actually reach the majority or even entirety of the said surface area, it may for economic reasons be useful to choose the porous adsorbent such that the specific surface area is at most 2500 or 2000 $m^2/g$.

The bringing into contact of the aqueous mixture with the porous adsorbent may be achieved by methods as such known to the skilled person. An example of such a method is the filling of a column with the porous adsorbent, followed by feeding the aqueous mixture to the column and forcing the mixture to flow through it. In this case, the porous adsorbent is preferably static or even fixed and the aqueous mixture is in movement.

As is known, it takes some time for an adsorption process to reach full equilibrium. Although waiting for full equilibrium may not always represent the most economical fashion for carrying out the process according the invention, it is still preferred that the adsorption step is carried out in such a fashion that a certain average contact time between porous adsorbent and aqueous mixture is achieved. Although the said contact time may vary within wide limits, it is preferred that it is at least 0.1 minute, so as to ensure that some adsorbing has taken place; preferably, the said average contact time is at least 0.5, 1, 2, 3, or even 5 minutes. For economical reasons, it is preferred to limit the average contact time to at most 150 minutes, preferably 140, 130, 120, 110 or 100 minutes.

The temperature and pressure at which the adsorption step are carried out may vary within wide limits, and are primarily dependent on choosing favourable conditions for carrying out the step in the most economical fashion. It will often not be necessary to operate at pressures other than atmospheric, although this is certainly possible. Likewise, temperatures other than room temperature are often not needed but certainly possible. It is noted hereby that an increase in temperature—e.g., from room temperature to 50° C.—is typically associated with a notable decrease in the amount of dipolar aprotic compound as adsorbed by the porous adsorbent.

Subsequent to the adsorption step a), the process according to the invention comprises a desorption step b). In the desorption step, the porous adsorbent is brought into contact with a desorbing agent. This implies that it should be ensured that the porous adsorbent is then essentially no longer in contact with the aqueous mixture; this may be done during the desorption step—e.g. by the act of bringing the desorbing agent in contact with the porous adsorbent—or prior to it. The purpose of the desorbing step is that the dipolar aprotic compound at least partly desorbs from the porous adsorbent and dissolves in or mixes with the desorbing agent.

As desorbing agent, any liquid is in principle suitable that, when brought into contact with the porous adsorbent, shows a lower equilibrium adsorption concentration of the dipolar aprotic compound as compared to that of the aqueous mixture. This lower equilibrium concentration provides the driving force for the desorbing activity. As will immediately be evident to the skilled person, the simple tests as described above for selecting a suitable porous adsorbent may also be used for determining whether a liquid is suitable as desorbing agent. Examples of compounds that may be comprised in the desorbing agent are: $C_1$-$C_4$ alkyl alcohols such as methanol and ethanol; $C_3$-$C_4$ iso-alkyl alcohols such as 2-propanol; ketones such as acetone; esters such as ethyl acetate; and water. The desorbing agent may also comprise a mixture of the said compounds. If the desorbing agent comprises or even consists essentially of water, then the water preferably has a temperature that is between 10° C. and 100° C. higher, more preferably between 20° C. and 70° C. higher than the temperature at which the adsorption step was carried out; it is possible to use water in the form of steam. In a preferred embodiment of the desorption step according to the invention, the desorbing agent comprises or even consists essentially of methanol.

During the execution of desorption step b), the desorbing agent has the effect that at least part of the dipolar aprotic compound as adsorbed to the porous adsorbent transfers into the desorbing agent, so that a new solution is being formed which is referred to herein as a recovery solution. The recovery solution comprises the desorbing agent and the dipolar aprotic compound. Furthermore, the recovery solution may comprise other compounds such as the compounds that were present in the aqueous mixture. The recovery solution may be separated from the porous adsorbent by simple means; an example thereof, in case the process according to the invention is carried out in such a way that the porous adsorbent and the desorbing agent have been brought together in a vessel, is the draining of the said vessel after completion of the desorption step. If the process according to the invention is carried out using a column filled with the porous adsorbent, the recovery solution may be collected at the outlet of the column. Preferably, however, use is made of the regeneration step as disclosed below for this purpose.

In a preferred embodiment of the process according to the invention, a replacement step a1) is executed after adsorption step a) and prior to desorption step b). In replacement step a1), the porous adsorbent is brought into contact with a replacement solution. The said replacement solution is preferably an aqueous solution containing less than 5 wt. %, preferably less than 2 wt. % of electrolytes based on the total weight of the replacement solution; furthermore, it is preferred that the replacement solution contains less than 20 wt. %, more preferably less than 10 wt. % or 5 wt. % of a compound or compounds that can act as desorbing agent.

Replacement step a1) is of interest in amongst others the case that the aqueous mixture contains compounds that do not dissolve in the desorbing agent. In such a case, the execution of the desorption step b) directly following adsorption step a) could lead to an accumulation of precipitated solid material in the porous adsorbent, which is undesirable. This issue may in certain circumstances be solved by simply separating the porous adsorbent from the aqueous mixture, e.g. by draining an adsorbent-containing column if the process according to the invention is carried out in such a way, followed by the desorption step. However, such a separating step could lead to the introduction of large volumes of gases such as air into the system wherein the process according to the invention is being carried out, which is often undesirable. For this reason, the execution of the said separation step is less preferred than the execution of the replacement step. As the skilled person will appreciate, the need to execute replacement step a1) depends on the specific nature of the compounds in the aqueous mixture and on the nature of the desorbing agent. If, for example, the desorbing agent comprises or even consists essentially of an alcohol such as methanol, then typical compounds that do not dissolve therein and thus could prompt the need for a separation step or more preferably a replacement step comprise various salts.

Since it is preferred for practical reasons that the replacement solution is miscible with the aqueous mixture, it is preferred that the replacement solution is an aqueous solution. In order to avoid the abovementioned precipitation problems during desorption step b), it is preferred that the replacement solution has a purity (related to water) in excess of 80 wt. %, preferably in excess of 90, 95 or even 99%, and contains less than 5 wt. %, preferably less than 2 wt. % of compounds that have a low solubility in the desorbing agent. Low solubility is defined herein as a solubility below 10 wt. % at room temperature.

In a preferred embodiment of the process according to the invention, a regeneration step c) is executed after desorption step b). The purpose of regeneration step c) is to bring the porous adsorbent in such a condition that the adsorption step a) can be executed in a better fashion—i.e. a quicker and/or a higher adsorption of the dipolar aprotic compound to the porous adsorbent—compared to when the regeneration step c) would not have been executed. In order to achieve this purpose, the porous adsorbent is brought into contact with a regeneration solution. The said regeneration solution is an aqueous solution containing less than 5 wt. %, preferably less than 2 wt. % of electrolytes based on the total weight of the regeneration solution; furthermore, it is preferred that the regeneration solution contains less than 20 wt. %, more preferably less than 10 wt. % or 5 wt. % of a compound or compounds that can act as desorbing agent. By bringing the porous adsorbent into contact with the regeneration solution, the recovery solution will at least be partly separated from the porous adsorbent. This is beneficial since this separation enables the isolation of the dipolar aprotic compound from the recovery solution.

In a further preferred embodiment of the process according to the invention, the desorption step b) or the regeneration step c) is followed by a recovery step d). In this recovery step d), the dipolar aprotic compound is isolated from the recovery solution. The said isolation may be achieved by methods that are as such known to the skilled person. Examples of such methods are rectification/distillation and/or thin-film evaporation. Since the concentration of the dipolar aprotic compound in the recovery solution will typically be much higher than in the said concentration in the aqueous mixture, the named technologies now have a much higher economical feasibility. It is advantageous to choose a desorbing agent which can be separated easily from the dipolar aprotic compound using the named technologies, e.g. by choosing a desorbing agent that either boils off very easily or has a higher boiling point than the dipolar aprotic compound.

In many cases, the practical implementation of the process according to the invention will involve the presence of a porous adsorbent in some sort of container, e.g. a stirred vessel or a column. In such cases, it will be possible to determine a Bed Volume (BV). BV is then defined as that part of the volume of the said container wherein the porous adsorbent resides. As is commonly done in processes for the treatment of aqueous mixtures, the amounts of the various streams as used—the aqueous mixture itself but also the desorbing agent and if applicable also the replacement solution and the regeneration solution—may be expressed in BV's, as such or per unit of time.

The number of BV's of aqueous solution that may be brought into contact with the porous adsorbent during the adsorption step before the adsorbent has reached its maximum capacity is, as the skilled person would expect, dependent on the initial concentration of the dipolar aprotic compound in the aqueous mixture and the adsorbing capacity of the porous adsorbent; the said number of BV's can be easily calculated from these two input data. If exceeding of the maximum adsorption capacity is to be avoided, e.g. in case of working with a column and when the presence of the dipolar aprotic compound at the exit of the column is undesirable, then the number of BV's of the aqueous mixture that is brought into contact with the porous adsorbent should remain below the maximum.

The number of BV's of desorbent is preferably chosen so that the concentration of dipolar aprotic compound in the recovery solution is as high as possible. This will often be the case by using between 0.5 and 2.0 BV's of desorbing agent, preferably between 0.75 and 1.5 BV's, most preferably between 0.8 and 1.2 BV's.

The number of BV's of replacement solution and regeneration solution is preferably as low as possible—while still being enough to fulfil in essence the objectives of the said solutions. This has the advantage that the concentration of valuable compounds in these solutions will be as high as possible so that a recovery of the said compounds is as efficient as possible. In preferred embodiments, the number of BV's as used of the replacement solution and the regeneration solution lies between 0.5 and 3.

An example in industry of an aqueous mixture suitable to be treated in the process according to the invention is a mixture that can be formed during the synthesis of 2-methyl-4-(2,6,6-trimethyl-1-cyclohexene-1-yl)-2-butenal, a $C_{14}$-aldehyde that is a valuable product in itself and furthermore an important intermediate in the synthesis of various products such as Vitamin A. The $C_{14}$-aldehyde may be prepared from â-ionone via an as such known Darzens-type of condensation as disclosed in a.o. U.S. Pat. No. 2,987,550. During this condensation process, it is advantageous to use a diluent, whereby it is surprisingly beneficial to use as a diluent a dipolar aprotic compound like DMSO, DMPU, TMU, or NMP. Furthermore, it is advantageous to use sodium methylate and the methyl ester of chloroacetic acid as reactants, as this leads to the formation of methanol as side-product, said methanol being a suitable desorbing agent. Subsequent to the condensation, a saponification step and hydrolysis step are carried out; this leads to a mixture being formed comprising a.o. the original diluent (e.g. DMSO, DMPU, TMU, or NMP), methanol and the $C_{14}$-aldehyde. The $C_{14}$-aldehyde may be removed from the mixture by means of an extraction step, whereby the extraction agent may be for example hexane. This then leads to the formation of a waste stream; the waste stream is an aqueous mixture comprising—besides water—methanol, the diluent and furthermore salts as formed during the previous steps, such as inorganic salts like NaCl and $NaHCO_3$ and organic salts such as $CH_3OCH_2COONa$ and/or $CH_3COONa$. The methanol can be isolated from the waste stream via rectification. It is then of high economic and ecologic interest to remove the diluent from this waste stream and to recover it; as the diluent is a dipolar aprotic compound, this may be achieved efficiently through the process of the invention, whereby there is an additional benefit of the potential to use methanol that was formed as desorbing agent, thereby limiting the number of compounds used in executing the synthesis of the $C_{14}$-aldehyde.

Another example of the use in industry of the process according to the invention is the treatment of aqueous mixtures that are formed for removing post-etch residues in the production of semiconductors; the forming of such aqueous mixtures containing a dipolar aprotic compound like NMP is disclosed in for example WO 2005/098920.

Yet a further example of the use in industry of the process according to the invention is the treatment of aqueous mixtures that are formed for, or during the stripping of paint. Also those mixtures commonly contain one or more dipolar aprotic compound which may be advantageously removed and preferably even recovered according to the invention.

The process according to the invention will be illustrated by means of the following Examples, without being limited thereto.

EXAMPLE 1

In order to assess whether Amberlite® XAD 4 (supplier: Rohm & Haas; this adsorbent comprises a matrix of a cross-linked polystyrene-divinylbenzene; the adsorbent is not further functionalised) is a suitable porous adsorbent, the following experiment was done. The adsorbent was rinsed thoroughly with deionised water. Then, 10 ml of the adsorbent was taken and put into 50 ml of a mixture of water and 4 wt. % of 1,1,3,3-tetramethylurea (TMU), under magnetic stirring. During this adsorption step, the temperature was kept at 25° C. After one hour under continued magnetic stirring, the amount of TMU in the water mixture was determined by means of gas chromatography (GC). The reduction of TMU concentration in the mixture allowed the determination of the amount of TMU that was adsorbed to the adsorbent, which was determined at 80 grams per liter of adsorbent.

EXAMPLE 2

Example 1 was repeated, with however the difference that the dipolar aprotic compound was 1-ethyl-2-pyrrolidone (NEP), initially present in the water in an amount of 3 wt. %. The amount of NEP as adsorbed by the adsorbent was determined at 57 grams per liter of adsorbent.

EXAMPLE 3

Example 2 was repeated, with however the difference that the porous adsorbent was Lewatit® VP OC 1064 (Supplier: Lanxess) and that NEP was initially present in the water in an amount of 2 wt. %. The amount of NEP as adsorbed by the adsorbent was determined at 42 grams per liter of adsorbent.

EXAMPLE 4

Example 1 was repeated, with however the difference that the porous adsorbent was Lewatit® VP OC 1163 (Supplier: Lanxess) and that the dipolar aprotic compound was 1,3-dimethyltetrahydro-2(1H)-pyrimidinone (DMPU), initially present in the water in an amount of 3 wt. %. The amount of DMPU as adsorbed by the adsorbent was determined at 170 grams per liter of adsorbent.

EXAMPLE 5

Example 1 was repeated, with however the difference that the dipolar aprotic compound was 1-methyl-2-pyrrolidone (NMP). The amount of NMP as adsorbed by the adsorbent was determined at 80 grams per liter of adsorbent.

EXAMPLE 6

Example 5 was repeated, with however the difference that the porous adsorbent was Dowex Optipore® L493 (supplier: Dow Chemical). The amount of NMP as adsorbed by the adsorbent was determined at 85 grams per liter of adsorbent.

EXAMPLE 7

Example 1 was repeated, with however the difference that the porous adsorbent was Lewatit® VP OC 1163 and the dipolar aprotic compound was NMP. The amount of NMP as adsorbed by the adsorbent was determined at 130 grams per liter of adsorbent.

EXAMPLE 8

In order to assess whether methanol is a suitable desorbing agent, the porous adsorbent Lewatit® VP OC 1163 was—after being thoroughly rinsed with deionised water—brought into contact with a methanol mixture consisting of 96 wt. % methanol and 4 wt. %—NMP under magnetic stirring. After one hour under continued magnetic stirring at 25° C., the amount of NMP in the methanol mixture was determined by means of gas chromatography (GC). The reduction of NMP concentration in the mixture allowed the determination of the amount of NMP that was adsorbed to the adsorbent, which was determined at 35 grams per liter of adsorbent. Since this amount is much lower than the equilibrium adsorption concentration of NMP in an aqueous system—see Example 1—it was thereby established that methanol can indeed serve as desorbing agent.

EXAMPLE 9

In order to execute adsorption step a) in combination with replacement step a1), desorption step b) with methanol as desorbing agent, and regeneration step c), the following laboratory-scale work was done.

A double-walled temperature-controlled chromatography-type glass column was filled with porous adsorbent Lewatit VP OC 1163; the adsorbent was kept as a fixed-bed. The column was about 450 mm long with an inner diameter of 26 mm; the bed volume (BV) was 0.178 liter adsorbent. The column was placed vertically; all liquids flowed from top to bottom with a throughput of 1 liter (or 5.6 BV) per hour. In order to execute the adsorption step, an aqueous stream with 20 grams per liter of the dipolar aprotic compound NMP dissolved in it and containing essentially no methanol was led through the column. The concentration of NMP was measured at the exit of the column. At the beginning of the adsorption step and during 50 minutes—or 4.7 BV—thereafter, the said concentration was zero, i.e. all of the NMP was adsorbed at the porous adsorbent. This established that the adsorption step was being done successfully. In the timeframe between 50 and 70 minutes, the concentration of NMP gradually increased to 20 grams per liter; this so-called breakthrough curve established that full saturation of the porous adsorbent had taken place and all NMP now passed through.

After the adsorbent had adsorbed the dipolar aprotic compound to the maximum extent, as determined via the breakthrough measurements, the replacement step a1) was done by changing the in-flow to de-ionised water. One bed-volume of de-ionised water was used; this ensured that any compounds not soluble in the desorbing agent were essentially removed. During this time the NMP concentration at the exit remained at about 20 grams per liter.

Subsequent to replacement step a1), the desorption step b) was executed by changing the in-flow of the column to methanol. 1.4 BV of methanol was used. The NMP was found to be readily desorbed from the porous adsorbent by the methanol, evidenced by a sharp increase of the NMP concentration at the exit to 130 grams per liter, then followed by a decline; the so-formed recovery solution was collected at the exit of the column and kept separate. The NMP concentration in the recovery solution was found to be 75 g/liter.

After completion of the desorption step b), the regeneration step c) was executed by changing the in-flow of the column to deionised water. About 2.5 BV of deionised water was used, so as to remove the methanol from the porous adsorbent. During this time, the NMP concentration at the exit decreased to essentially zero. The column was thus regenerated and ready for execution of step a) of a renewed cycle.

EXAMPLE 10

In order to execute adsorption step a) in combination with replacement step a1), desorption step b) with methanol as desorbing agent, regeneration step c), and recovery step d), the following pilot-plant work was done.

A stainless steel column was filled with porous adsorbent Lewatit® VP OC 1163; the adsorbent was kept as a fixed-bed. The column was somewhat more than 2000 mm long with an inner diameter of 109.1 mm; the inner bed volume (BV) was 18.7 liter. The column was placed vertically; the liquids flowed from top to bottom with a throughput of 93.5 liter (or 5 BV) per hour during the adsorption step a) and with a throughput of 46.7 liter (or 2.5 BV) per hour in all other steps.

In order to execute the adsorption step, 10 BV of an aqueous mixture was fed to the column. The aqueous mixture was formed in a process for the preparation of the $C_{14}$-aldehyde 2-methyl-4-(2,6,6-trimethyl-1-cyclohexene-1-yl)-2-butenal and had the following composition: water 92.3 wt. %, NMP 1.2 wt. %, electrolytes (salts) 5.5 wt. %, NaOH 0.7 wt. %, rest impurities 0.3 wt. %. It was found typically that breakthrough began after 7-7.5 BV and was full after 9-9.5 BV.

Replacement step a1) was executed by changing the feed to deionised water and feeding 1 BV.

Subsequent to replacement step a1), the desorption step b) was executed by changing the in-flow of the column to methanol. 1.5 BV of methanol was used. The so-formed recovery solution was collected at the exit of the column and kept separate. The NMP concentration in the recovery solution was found to be 8.5 wt. %.

After completion of the desorption step b), the regeneration step c) was executed by changing the in-flow of the column to deionised water. 2 BV of deionised water was used, so as to remove the methanol from the porous adsorbent. During this time, the NMP concentration at the exit decreased to essentially zero, indicating that all of the NMP had left the column. The column was thus regenerated and ready for execution of step a) of a renewed cycle.

The recovery solution was, in order to execute recovery step d), fed to a distillation column. The top product consisted of 89.2 wt. % methanol, 10.8 wt. % water and essentially no NMP. The bottom product consisted of 0.1 wt. % water, 80.4 wt. % NMP and 18.5 wt. % of various impurities resulting from the preparation of the $C_{14}$ aldehyde. The bottom product was fed to a thin-film evaporator; the top product consisted of NMP with about 2 wt. % of impurities. This product could be re-used successfully for the process of preparation of the $C_{14}$-aldehyde.

The invention claimed is:

1. A process for the treatment of an aqueous mixture comprising a dipolar aprotic compound which is selected from the group consisting of hexamethylphosphorous triamide (HMPT), dimethylsulfoxide (DMSO), 1-ethyl-2-pyrrolidone (NEP) and urea derivatives of the following formula:

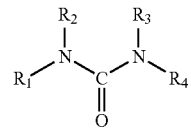

wherein $R_1$, $R_2$, $R_3$ and $R_4$ may each independently be H or a $C_1$-$C_4$ alkyl group and wherein $R_2$ and $R_3$ may be part of a heterocyclic group, the process comprising:

a) an adsorption step which comprises bringing the aqueous mixture into contact with a porous adsorbent, wherein the porous adsorbent is chosen such that the dipolar aprotic compound adsorbs to it more readily than water; and b) a desorption step which comprises bringing the porous adsorbent into contact with a desorbing agent which comprises methanol to thereby form a recovery solution comprising the desorbing agent and the dipolar aprotic compound.

2. A process for the treatment of an aqueous mixture comprising a dipolar aprotic compound which is selected from the group consisting of hexamethylphosphorous triamide (HMPT), dimethylsulfoxide (DMSO), 1-methyl-2-pyrrolidone (NMP), 1-ethyl-2-pyrrolidone (NEP) and urea derivatives of the following formula:

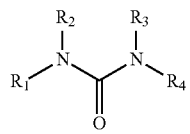

wherein $R_1$, $R_2$, $R_3$ and $R_4$ may each independently be H or a $C_1$-$C_4$ alkyl group and wherein $R_2$ and $R_3$ may be part of a heterocyclic group, the process comprising:
a) an adsorption step which comprises bringing the aqueous mixture into contact with a porous adsorbent, wherein the porous adsorbent is chosen such that the dipolar aprotic compound adsorbs to it more readily than water; and
b) a desorption step which comprises bringing the porous adsorbent into contact with a desorbing agent which comprises methanol to thereby form a recovery solution comprising the desorbing agent and the dipolar aprotic compound, wherein
the process further comprises after step a) and prior to step b):
a1) a replacement step which comprises bringing the porous adsorbent into contact with a replacement solution, said replacement solution being an aqueous solution containing at most 5 wt. % of electrolytes based on the total weight of the replacement solution and at most 20 wt. % of a compound or compounds that can act as desorbing agent.

3. A process for the treatment of an aqueous mixture comprising a dipolar aprotic compound which is selected from the group consisting of hexamethylphosphorous triamide (HMPT), dimethylsulfoxide (DMSO), 1-methyl-2-pyrrolidone (NMP), 1-ethyl-2-pyrrolidone (NEP) and urea derivatives of the following formula:

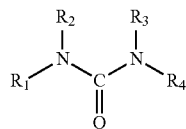

wherein $R_1$, $R_2$, $R_3$ and $R_4$ may each independently be H or a $C_1$-$C_4$ alkyl group and wherein $R_2$ and $R_3$ may be part of a heterocyclic group, the process comprising:
a) an adsorption step which comprises bringing the aqueous mixture into contact with a porous adsorbent, wherein the porous adsorbent is chosen such that the dipolar aprotic compound adsorbs to it more readily than water; and
b) a desorption step which comprises bringing the porous adsorbent into contact with a desorbing agent which comprises methanol to thereby form a recovery solution comprising the desorbing agent and the dipolar aprotic compound, wherein
the process further comprises subsequent to step b):
c) a regeneration step which comprises bringing the porous adsorbent into contact with a regeneration solution, said regeneration solution being an aqueous solution containing at most 5 wt. % of electrolytes based on the total weight of the replacement solution and at most 20 wt. % of a compound or compounds that can act as desorbing agent, whereby the recovery solution is at least partly separated from the porous adsorbent.

4. A process for the treatment of an aqueous mixture comprising a dipolar aprotic compound which is selected from the group consisting of hexamethylphosphorous triamide (HMPT), dimethylsulfoxide (DMSO), 1-methyl-2-pyrrolidone (NMP), 1-ethyl-2-pyrrolidone (NEP) and urea derivatives of the following formula:

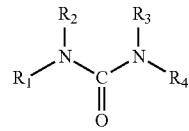

wherein $R_1$, $R_2$, $R_3$ and $R_4$ may each independently be H or a $C_1$-$C_4$ alkyl group and wherein $R_2$ and $R_3$ may be part of a heterocyclic group, the process comprising:
a) an adsorption step which comprises bringing the aqueous mixture into contact with a porous adsorbent, wherein the porous adsorbent is chosen such that the dipolar aprotic compound adsorbs to it more readily than water; and
b) a desorption step which comprises bringing the porous adsorbent into contact with a desorbing agent which comprises methanol to thereby form a recovery solution comprising the desorbing agent and the dipolar aprotic compound, wherein
the process further comprises subsequent to step b) or c):
d) a recovery step which comprises isolating the dipolar aprotic compound from the recovery solution.

5. Process according to claim 1, 2, 3 or 4, wherein the porous adsorbent comprises a cross-linked resin.

6. Process according to claim 5, wherein the porous adsorbent has a specific surface area of at least 400 m²/g.

7. Process according to claim 5, wherein the porous adsorbent comprises a cross-linked polystyrene-divinylbenzene resin.

* * * * *